United States Patent [19]

Godek et al.

[11] Patent Number: 5,294,744
[45] Date of Patent: Mar. 15, 1994

[54] FORMYLATION PROCESS FOR AROMATIC ALDEHYDES

[75] Inventors: Dennis M. Godek, Glastonbury; William M. Synder, New London; Andrew M. Stewart, North Stonington, all of Conn.

[73] Assignee: Pfizer Inc., New York, N.Y.

[21] Appl. No.: 49,904

[22] Filed: Apr. 20, 1993

[51] Int. Cl.⁵ .......................................... C07C 47/575
[52] U.S. Cl. ................................. 568/442; 568/425; 568/426
[58] Field of Search ................... 568/425, 426, 442

[56] References Cited

U.S. PATENT DOCUMENTS 4,192,949  3/1980  Merger et al. .................... 560/67
4,515,987  5/1985  Boden et al. ..................... 568/442

OTHER PUBLICATIONS

W. E. Smith, *Journal of Organic Chemistry*, vol. 37, No. 24, p. 3972 (1972).

Primary Examiner—Werren B. Lone
Attorney, Agent, or Firm—Peter C. Richardson; Paul H. Ginsburg

[57] ABSTRACT

A novel two-step reaction process for preparing 5-substituted-2-methoxybenzaldehyde compounds is disclosed wherein the substituent group is either isopropyl or trifluoromethoxy. The process involves (1) reacting a corresponding 4-substituted phenol compound with dimethyl carbonate in the presence of a tertiary-amine base to form the corresponding 4-substituted anisole compound, and (2) thereafter subjecting the latter intermediate product obtained in the first step to aromatic C-formylation on the ring with hexamethylenetetramine in the presence of trifluoroacetic acid, followed by hydrolysis, to ultimately yield the desired aldehyde compound. The two aromatic aldehyde compounds so obtained, viz., 2-methoxy-5-trifluoromethoxybenzaldehyde and 2-methoxy-5-isopropylbenzaldehyde, are known to be useful as intermediates that specifically lead to (2S,3S)-cis-3-(2-methoxy-5-trifluoromethoxybenzyl)amino-2-phenylpiperidine and (2S,3S)-cis-2-(diphenylmethyl)-N-[(2-methoxy-5-isopropylphenyl)-methyl]-1-azabicyclo[2.2.2]octane-3-amine, respectively. The latter final products, in turn, are both known to be useful in the field of medicinal chemistry as substance P receptor antagonists.

10 Claims, No Drawings

FORMYLATION PROCESS FOR AROMATIC ALDEHYDES

BACKGROUND OF THE INVENTION

This invention relates to a new and useful process for preparing aromatic aldehydes by the direct introduction of the formyl group into a benzene ring system. More particularly, it is concerned with a novel two-step method for synthesizing a 5-substituted-2-methoxybenzaldehyde compound wherein the substituent group is either isopropyl or trifluoromethoxy. These two aldehyde compounds are known to be of value as intermediates that lead to certain substance P receptor antagonists.

In accordance with the prior art, there has already been described certain compounds which are known to be of value as substance P receptor antagonists. Included among these are such nitrogen-containing heterocyclic ring compounds as (2S,3S)-cis-3-(2-methoxy-5-trifluoromethoxybenzyl)amino-2-phenylpiperidine, which is described and claimed by J. A. Lowe, III et al., in Published P.C.T. International Patent Application No. WO 93/00331 (published Jan. 7, 1993) and (2S,3S)-cis-2-(diphenylmethyl)-N-[(2-methoxy-5-isopropylphenyl)methyl]-1-azabicyclo[2.2.2]octane-3-amine, which is described and claimed by F. Ito et al., in Published P.C.T. International Patent Application No. WO 92/21677 (published Dec. 10, 1992). Both compounds are useful as non-steroidal anti-inflammatory (N.S.A.I.) agents, being of specific value in the treatment of arthritis, asthma and inflammatory bowel disease.

In the past, these particular compounds have been prepared by various synthetic means but essentially by a method which involves the reductive amination of the appropriate aldehyde compound, i.e., by reacting either 2-methoxy-5-isopropylbenzaldehyde or 2-methoxy-5-trifluoromethoxybenzaldehyde, as the case may be, with the corresponding heterocyclic 3-amino compound in the presence of a source of hydrogen, or else by first condensing the aforesaid 3-amino compound with the aldehyde and then reducing the resulting imine intermediate to ultimately give the key benzylamine side chain. The starting aromatic aldehyde component in this particular reaction scheme had always been prepared in two steps starting from the corresponding known and readily available 4-substituted phenol compound and this, in turn, initially involved (1) first methylating the phenol compound with methyl iodide in an acetone solvent medium in the presence of solid potassium carbonate, followed by (2) direct formylation of the resulting 4-substituted methylated phenol (i.e., 4-substituted anisole compound) with α,α-dichloromethyl methyl ether in a methylene chloride solvent system in the presence of titanium tetrachloride as catalyst. However, this particular two-step method for the production of the aldehyde suffers from the drawback of being conducted in a non-homogenous reaction system in the first step, with all its attendant disadvantages, and in employing the somewhat hazardous titanium tetrachloride reagent as catalyst in the second step. In the latter connection, it should be noted that certain stringent safety requirements are normally called for when handling the latter agent, particularly when unit operations are conducted on a large scale. Additionally, the use of various hazardous waste disposal techniques are also required for the removal of the titanium tetrachloride byproducts that are usually formed in the aforesaid aromatic formylation reaction.

In the past, F. Merger et al. in U.S. Pat. No. 4,192,949 indicate that they have prepared various methyl phenyl ethers, including both 4-methylanisole and 4-methoxyanisole, from the corresponding phenol compounds, using dimethyl carbonate in the presence of a tertiary-amine base as catalyst without the presence of a solvent. Although the Merger et al. patent also includes p-isopropylphenol in a long list of many other possible phenolic starting materials for the aforementioned reaction, there is no indication that 4-isopropylanisole was ever actually prepared in this particular manner. On the other hand, W. E. Smith in the *Journal of Organic Chemistry*, Vol. 37, No. 24, p. 3972 (1972) reports on the direct C-formylation of several aromatic compounds, including 2,6-dimethylanisole, via a method which involves the use of hexamethylenetetramine in trifluoroacetic acid in a modified Duff reaction, but there is no indication in the aforesaid paper by Smith that such a reaction could ever be successfully carried out using other non-acidic derivatives of anisole as substrate. In particular, there is no indication that the reaction of Smith could be applied to parasubstituted derivatives of anisole.

SUMMARY OF THE INVENTION

In accordance with the present invention, there is now provided a new and improved process for preparing 5-substituted-2-methoxybenzaldehyde compounds of the type previously discussed in pure form and in high yield by employing a novel two-step reaction sequence, starting from the corresponding known 4-substituted phenol wherein the substituent group is either isopropyl or trifluoromethoxy. More particularly, the novel two-step process of this invention concerns a process for preparing a 5-substituted-2-methoxybenzaldehyde compound having the formula:

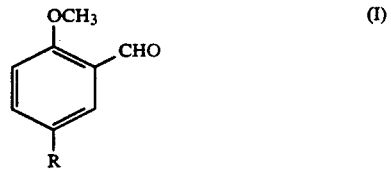

(I)

wherein R is isopropyl or trifluoromethoxy, which comprises the steps of (a) reacting a corresponding 4-substituted phenol compound of the formula:

(II)

wherein R is as hereinbefore defined, with dimethyl carbonate in the presence of a tertiary-amine base and in the presence or absence of a reaction-inert polar organic solvent, with the proviso that said solvent is always present when R is isopropyl, with said reaction being conducted at a temperature that is in the range of from about 120° C. up to about 170° C. until the O-methylation reaction to form the corresponding 4-substituted anisole compound of the formula:

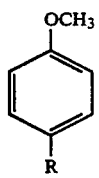

(III)

wherein R is as previously defined, is substantially complete; and (b) thereafter subjecting the intermediate 4-substituted anisole compound of the formula III obtained in step (a) to aromatic C-formylation on the ring with hexamethylenetetramine in the presence trifluoroacetic acid at a temperature that ranges from between about 65° C. and the reflux temperature of the reaction mixture until the aminoalkylation reaction is substantially complete, followed by hydrolysis of the resulting mixture at ambient temperatures to ultimately yield the desired aldehyde compound of structural formula I.

In this way, a compound such as 4-trifluoromethoxyphenol is readily converted, via the known intermediate 4-trifluormethoxyanisole, to 2-methoxy-5-trifluoromethoxybenzaldehyde in a most facile manner without incurring any of the previously mentioned disadvantages normally associated with the prior art techniques. In like manner, 4-isopropylphenol is converted, via the known intermediate 4-isopropylanisole, to 2-methoxy-5-isopropylbenzaldehyde in an equally facile way. As previously indicated, the two final products produced by the novel two-step reaction process of the present invention, viz., 2-methoxy-5-trifluoromethoxybenzaldehyde and 2-methoxy-5-isopropylbenzaldehyde, are both useful compounds as valuable intermediates that ultimately lead to the key medicinal final products that are known as substance P receptor antagonists.

DETAILED DESCRIPTION OF THE INVENTION

In accordance with the process of this invention, the initial stage (a) of the novel two-step reaction sequence for preparing the desired 5-substituted-2-methoxybenzaldehyde compound of formula I, wherein R is either isopropyl or trifluoromethoxy, involves first methylating a corresponding phenol compound of the formula II with dimethyl carbonate in the presence of a tertiary-amine base and in the presence or absence of a reaction-inert polar organic solvent, except that the solvent must always be present when R is isopropyl, at a temperature that is in the range of from about 120° C. up to about 170° C., and preferably one that lies within the range of about 130°-155° C., until the desired O-methylation reaction to form the corresponding 4-substituted anisole compound of the formula III, wherein R is defined as aforesaid, is substantially complete. This initial reaction step will generally require a period of at least about two hours. Although the aforesaid methylation step is readily accomplished with or without a solvent when R is trifluoromethoxy, as previously mentioned, it is most preferably carried out in the absence of a solvent when R is trifluoromethoxy and most assuredly in the presence of a reaction-inert polar organic solvent when R is isopropyl. Preferred reaction-inert polar organic solvents for use in this connection include such solvents as dimethyl sulfoxide, dimethylformamide, dimethylacetamide and the like. The methylation step also calls for the use of an organic tertiary-amine base as catalyst to assist the reaction, as this particular agent tends to shift the reaction equilibrium to completion. Preferred organic tertiary-amine bases for use in this connection include trimethylamine, p-dimethylaminoaniline and most especially, 4-dimethylaminopyridine. In general, the molar ratio of the phenolic starting material of structural formula II employed in the reaction to the dimethyl carbonate reagent in step (a) is one that lies within the range of from about 1.0:1.0 to about 1.0:5.0, respectively, with the preferred range being in the neighborhood of about 1.0:1.5 to about 1.0:2.0 for the present purposes at hand. The amount of tertiary-amine base employed in said step, on the other hand, ranges from about 20 mole percent up to about 80 mole percent, based on the total molar amount of phenolic starting material of formula II, with the preferred amounts being in the range of about 25-60 mole percent. Upon completion of the methylation reaction step, the desired 4-substituted anisole compound of the formula III is then readily recovered from the spent reaction mixture by any number of conventional techniques that are well-known to those skilled in the art (see Examples 1-2 for details).

The second and final stage of the novel two-step reaction process of the present invention is concerned with converting the intermediate 4-substituted anisole compound of the formula III obtained in step (a) to a corresponding 5-substituted 2-methoxybenzaldehyde compound of the formula I via a facile and direct formylation procedure that involves the use of hexamethylenetetramine in conjunction with trifluoroacetic acid. More particularly, the second step (b) of the claimed reaction process involves subjecting the intermediate 4-substituted anisole compound of the formula III, wherein R is isopropyl or trifluoromethoxy, as previously obtained in step (a), to aromatic C-formylation on the ring by initially reacting said anisole compound at the desired ortho-position with hexamethylenetetramine in the presence of trifluoroacetic acid at a temperature that ranges from between about 65° C. and the reflux temperature of the reaction mixture until the ortho-substitution reaction is substantially complete, followed by hydrolysis of the resulting mixture at ambient temperatures to ultimately yield the desired aldehyde compound of structural formula I. In general, the molar ratio of the 4-substituted anisole compound of structural formula III, which serves as the starting material for this particular reaction step, to the hexamethylenetetramine reagent is one that lies within the range of from about 4.0:1.0 to about 1.0:2.0, respectively, with the preferred molar ratio range being in the neighborhood of about 1.0:1.0. In a preferred embodiment of this particular reaction step, the 4-substituted anisole compound is first made to react with the hexamethylenetetramine reagent on what is essentially an equimolar basis and in the presence of trifluoroacetic acid as both the acid catalyst and the solvent. This particular reaction is normally conducted at a temperature that lies within the more preferred temperature range that is from about 65° C. up to about 100° C. for a period of time that is at least about four hours. Preferred reaction conditions usually call for a temperature that is preferably one that lies within the temperature range of from about 70° C. up to about 90° C. for a period of time that is at least about six hours (and most preferably, for from about six to about 14 hours). Upon completion of the initial ortho-substitution reaction, the resulting reaction mixture is thereafter subjected to hydrolysis at ambient temperatures by the addition of water thereto and the desired 1-aldehyde compound is subsequently isolated from the final mixture in a most conventional manner. For example, the trifluoroacetic acid solvent is first removed from the spent reaction mixture via evaporation under reduced pressure, and the resulting residual oil is thereafter basified with aqueous sodium hydroxide solution in order to effect a pH adjustment to a value in the neighborhood of pH 9.0, followed by a subsequent extraction of the aqueous system with a water-immiscible organic solvent like hexane or methylene chloride, etc., in order to effectively isolate the pure organic product from the aforesaid aqueous system.

The 4-substituted phenol compounds of formula II required as the ultimate starting materials for conducting the novel overall two-step reaction process of this invention are both known compounds that are either readily available commercially or else they can easily be synthesized by those skilled in the art starting from common organic chemical reagents and by using conventional methods of organic synthesis. This same situation also holds true for all the other reactants and reagents employed in the novel two-step process, such as dimethyl carbonate and 4-dimethylaminopyridine employed in the first step (a) and hexamethylenetetramine and trifluoroacetic acid as used in the second step (b).

As previously indicated, the 5-substituted 2-methoxybenzaldehyde final products afforded by the novel two-step reaction process of the present invention, viz., 2-methoxy-5-trifluoromethoxybenzaldehyde and 2-methoxy-5-isopropylbenzaldehyde, are both known to be useful as valuable intermediates that ultimately lead to the two substance P receptor antagonists known as (2S,3S)-cis-3-(2-methoxy-5-trifluoromethoxybenzyl)amino-2-phenylpiperidine and (2S,3S)-cis-2-(diphenylmethyl)-N-[(2-methoxy-5-isopropylphenyl)methyl]-1-azabicyclo[2.2.2.]octane-3-amine, respectively, by using the standard methods earlier disclosed in the aforementioned prior art. More specifically, J. A. Lowe III et al., in Published P.C.T. International Patent Application No. WO 93/00331 (published Jan. 7, 1993) refer to the reaction of 2-methoxy-5-trifluoromethoxybenzaldehyde in glacial acetic acid with 3-amino-2-phenylpiperidine in the presence of sodium triacetoxyborohydride to give (2S,3S)-cis-3-(2-methoxy-5-trifluoromethoxybenzyl)amino-2-phenylpiperidine (see Example 5 for details), while F. Ito et al. in Published P.C.T. International Patent Application No. WO 92/21677 (published Dec. 10, 1992) refer to the reaction of 2-methoxy-5-isopropylbenzaldehyde in methylene chloride with (2S,3S)-2-(diphenylmethyl)-1-azabicyclo[2.2.2.]octane-3-amine in the presence of sodium triacetoxyborohydride to afford (2S,3S)-cis-2-(diphenylmethyl)-N-[(2-methoxy-5-isopropylphenyl)methyl]-1-azabicyclo[2.2.2.]octane-3-amine (see Example 6 for details).

Hence, the novel process of the present invention now provides 2-methoxy-5-trifluoromethoxybenzaldehyde and 2-methoxy-5-isopropylbenzaldehyde, as discussed above, in pure form and in high yield by a unique two-step synthetic method, which represents a major improvement over the previously-discussed prior art procedures in view of the ease of synthesis and the reduced costs involved in the overall method production. More specifically, it circumvents the use of titanium tetrachloride as a catalytic agent in the formylation step with all its potential hazards and, in addition, it also allows the initial methylation step to proceed smoothly and under normally homogenous reaction conditions, thereby avoiding the need to work with often bulky and cumbersome suspensions during the course of the required unit operations.

EXAMPLE 1

To a 12-L three-necked, round-bottom reaction flask equipped with thermometer, reflux condenser, addition funnel and mechanical stirring apparatus, there were placed 2.5 Kg (14 moles) of 4-trifluoromethoxyphenol (available from the Central Glass Company, Ltd. of Tokyo, Japan) and 1.5 Kg (7.8 moles) of 4-dimethylaminopyridine at ambient temperatures (ca. 20° C.), with stirring being maintained throughout the course of the entire mixing step. The resulting reaction mixture than exothermed to 29° C. and was thereafter externally heated to 150° C. When the pot temperature eventually reached 152° C., there was then slowly added to the stirred mixture a total amount of 1.9 Kg (21 moles) of dimethyl carbonate in a dropwise manner over a 12-hour period. When the aforesaid addition step was adjudged to be complete, all the initial starting materials has already been observed to be completely consumed by the entire reaction mixture. The course of the aforesaid methylation reaction was followed throughout by means of thin layer chromatography (TLC) and the rate of reagent addition was controlled in such a way as to always maintain a pot temperature of more than 130° C. The vapors in the head space were also distilled at such a rate as to assist in maintaining a pot temperature of greater than 130° C. Upon completion of the desired O-methylation reaction as evidenced by TLC analysis (eluant: hexanes/ethyl acetate, 9:1 by volume; 254 mm), the spent reaction mixture was slowly allowed to cool to ambient temperatures. At this point (about nine hours in time had elapsed from the point where the heat was initially terminated), 2.5 L of hexanes and 4.5 L of water were added to the cooled final mixture. The diluted mixture was next transferred to a 22-L three-necked, round-bottomed reaction flask and subsequently treated with an additional 4 L of hexanes and 4 L of water, followed by 900 g of activated charcoal with stirring. After stirring the treated mixture for a period of 1.5 hours, it was subsequently filtered through celite and the recovered filter cake of carbon was thereafter washed with a fresh portion of hexanes. The resulting two-phase filtrate was then separated into its component parts and 1.5 L of water was subsequently added to the separated layer of hexanes, followed by a pH adjustment thereto of from pH 11.87 to pH 3.0 with added 3N hydrochloric acid.

The two layers were again next separated, followed by the introduction of 500 g of freshly-activated charcoal into the newly-separated hexanes layer. The treated mixture was then stirred for a period of one hour, filtered through celite and the recovered filter cake subsequently washed with an additional fresh portion of hexanes to finally give a clear organic solution as the filtrate. After drying the latter filtrate over 400 g of anhydrous sodium sulfate for a period of 16 hours, the dried filtrate was next passed through celite to remove the drying agent and subsequently stripped of solvent by means of evaporation under reduced pressure to ultimately yield 1.6 Kg (59%) of pure 4-trifluoromethoxyanisole in the form of a residual oil. The pure product was subsequently characterized by means of nuclear magnetic resonance (NMR) data.

NMR Data: $^1$H NMR(CDCl$_3$) δ3.8(s, 3H), 6.88(d, 2H), 7.17(d, 2H).

EXAMPLE 2

To a well-stirred solution consisting of 2.5 Kg (18.4 moles) of 4-isopropylphenol (available from the Aldrich Chemical Company, Inc. of Milwaukee, Wis.) dissolved in 2.5 L of dimethyl sulfoxide at 20°-25° C., there were added 560 g (4.6 moles) of 4-dimethylaminopyridine. The resulting solution was then heated to 135° C., at which point a total of 3.3 Kg (36.6 moles; 3.1 L) of dimethyl carbonate were next added slowly to the stirred mixture over a 4.5-hour period, while keeping the reaction temperature between 135°-153° C. throughout the entire addition period. Upon completion of this step, thin layer chromatography (TLC) assessment of the reaction mixture (using the same solvent system for eluant as was earlier employed in Example 1) showed no evidence of any remaining starting material for the present purposes at hand, but rather revealed evidence of a less polar component. The spent reaction mixture was next cooled to a temperature below 100° C. and subsequently diluted with 10 L of water, followed by a further cooling to 30° C. and immediately thereafter by the addition of 8 L of hexanes. The pH was then re-adjusted from a value of pH 10.3 to pH 3.0 with 12 L of added 3N hydrochloric acid, and the resulting aqueous/organic mixture was thereafter filtered through celite and the two layers subsequently allowed to settle and separate.

The separated aqueous layer was next washed with four-1.0 L portions of hexanes, and the resulting organic layers were thereafter combined and treated with 125 g of activated charcoal and 400 g of anhydrous magnesium sulfate. The treated organic mixture was then stirred for a period of one hour, filtered though celite and the recovered filter cake subsequently washed with a fresh portion of hexanes to give a clear dry solution as the filtrate. Concentration of the latter solution in vacuo then gave 2.4 Kg (83%) of pure 4-isopropylanisole as the residual oil. The pure product was subsequently characterized by means of nuclear magnetic resonance (NMR) data.

NMR Data: $^1$H NMR (CDCl$_3$) δ1.25(d, 6H), 2.9(m, 1H), 3.8(s, 3H), 6.88(d, 2H), 7.18(d, 2H).

EXAMPLE 3

To each of two-separate 22-L three-necked, round-bottomed reaction flasks equally equipped with a thermometer, reflex condenser and mechanical stirrer, there were added 800 g (4.2 moles) of 4-trifluoromethoxyanisole (the product of Example 1) and 10.5 L of trifluoroacetic acid at ambient temperatures (ca. 20° C.) with constant agitation being maintained throughout the course of the entire addition step. This was followed by the slow addition of 600 g (4.3 moles) of hexamethylenetetramine in small amounts to the well-stirred mixture now contained in each of the two reaction flasks. The resulting reaction mixture in each reaction flask then exothermed from 22° C. to 38° C. in each instance and was thereafter externally heated to the reflux temperature of the reaction mixture, using a pot temperature of ca. 80° C. for this purpose. The stirred and heated reaction mixture was then refluxed for a period of 12.5 hours, while the course of the aromatic formylation reaction was followed by means of thin layer chromatography (TLC) in the usual manner. At the end of the eleven-hour mark, the reaction appeared to be essentially complete as evidenced by the TLC analysis (eluant: hexanes/ethyl acetate, 9:1 by volume, 254 nm). Upon final completion of the aforesaid reflux step, the two-separate spent reaction mixtures so obtained were then combined and subsequently concentrated at atmospheric pressure in a single 22-L three-necked, round-bottomed reaction flask to a volume of approximately 8 L, using a pot temperature of 85° C. At this point, the partially concentrated final reaction mixture was further concentrated in vacuo to an oil, using a pot temperature of 55° C. and the residual oil was thereafter divided into two equal halves and each half thereafter placed in two-separate 22-L three-necked, round-bottomed reaction flasks (with each flask containing approximately 4 L of oil).

Each flask containing the stirred oil then received 4 L of methylene chloride, followed by the addition of 4 L of water over a 20-minute period with no discernable exotherm to the resulting aqueous organic system. The pH of the latter was then re-adjusted from pH 0.1 to a new value of pH 9.0 with 3.6 L of added 20% aqueous sodium hydroxide solution. The two separately-basified two-phase systems were next transferred from each reaction flask to two-different separatory funnels corresponding to same, and the two respective separate layers were subsequently allowed to settle before separating and removing the methylene chloride layers from the aqueous layers. The two-saved aqueous layers were then each extracted with 4 L of methylene chloride, and the combined methylene chloride layers were next washed with 8 L of water and thereafter dried over 1.0 Kg of anhydrous magnesium sulfate for a period of one-half hour. After removal of the drying agent by means of suction filtration and careful washing of the resulting filter cake with 2 L of fresh methylene chloride, the resulting organic filtrate was subsequently concentrated in vacuo to afford 1.7 Kg (91%) of pure 2-methoxy-5-trifluoromethoxybenzaldehyde in the form of a residual yellow oil. The pure product was characterized by means of nuclear magnetic resonance (NMR) data.

NMR Data: $^1$H NMR(CDCl$_3$) δ3.95(s, 3H), 7.0(d, 1H), 7.43(dd, 1H), 10.4(s, 1H).

EXAMPLE 4

To each of two-separate 22-L three-necked, round-bottomed reaction flasks equally equipped with thermometer, reflux condenser and mechanical stirrer, there were charged 1.3 Kg (7.4 moles) of 4-isopropylanisole (the product of Example 2) and 12.0 L of trifluoroacetic acid at ambient temperatures (ca. 20° C.) with constant agitation being maintained throughout the course of the entire addition step. This was then followed by the slow addition of 1.0 Kg (7.4 moles) of hexamethylenetetramine in small portions over a 50-minute period to the two well-stirred reaction mixtures now contained in each of the two-separate reaction flasks. The resulting reaction mixture in each flask then exothermed from 24° C. to 38° C. in each instance and was thereafter externally heated up to the reflux temperature of the reaction mixture at 81° C. The stirred and heated reaction mixture was next refluxed at this point for a period of 14 hours. Upon completion of this step, the trifluoroacetic acid solvent was removed from each of the two spent reaction mixtures via concentration under reduced pressure and each resulting residual oil was thereafter partitioned between 4 L of water and 4 L of hexanes. The pH of the two-phase system now contained in each flask was subsequently re-adjusted from a pH value of 0.5 to a value of pH 9.0 by adding thereto separate-3.8 L and 4.2 L portions of 6N aqueous sodium hydroxide solution, respectively. The basified two-phase systems were then allowed to settle and separate, and the two-separated aqueous layers were thereafter saved and subsequently washed with a fresh 2 L-portion of hexanes. The organic layers were next combined and subsequently backwashed with 3 L of water, followed by treatment with 200 g of activated charcoal and 400 g of anhydrous magnesium sulfate as drying agent. After removal of the latter two substances by means of suction filtration through celite, the resulting clear organic filtrate was subsequently concentrated in vacuo to give 2.0 Kg (72%) of crude aldehyde final product in the form of a dark residual oil. The latter material (1.8 Kg) was then purified by means of distillation in vacuo to ultimately afford 880 g (44%) of pure 2-methoxy-5-isopropylbenzaldehyde. The pure product was characterized by means of nuclear magnetic resonance (NMR) data.

NMR Data: $^1$H NMR(CD$_3$OD) δ1.05(d, 6H), 2.74(m, 1H), 3.75(s, 3H), 6.95(d, 1H), 7.35(dd, 1H), 7.35(dd, 1H), 7.5 1H, 10.23(s, 1H).

EXAMPLE 5

In a round-bottomed reaction flask equipped with reflux condenser, magnetic stirrer and nitrogen-inlet tube, there were placed 350 mg (0.0020 mole) of (2S,3S)-3-amino-2-phenylpiperidine (prepared according to the procedure described by J. A. Lowe III et al., in aforementioned Published P.C.T. International Patent Application No. WO 93/00331) and 525 mg (0.0024 mole) of 2-methoxy-5-trifluoromethoxybenzyaldehyde (the product of Example 3) in 5 ml of glacial acetic acid, while under a dry nitrogen atmosphere. Stirring was then commenced and after a period of one hour at room temperature (ca. 20° C.), the well-stirred organic solution was treated with 933 mg (0.0044 mole) of sodium triacetoxyborohydride which was added in small, divided portions. The resulting reaction mixture was next stirred at room temperature for a period of three days and thereafter concentrated with the aid of a rotary evaporator. The residue so obtained was then partitioned between 1N aqueous sodium hydroxide solution and chloroform, followed by separation of the two resulting layers and further extraction of the separated aqueous phase with three portions of fresh chloroform. The combined chloroform extracts were next extracted with three portions of 1N aqueous hydrochloric acid. The combined aqueous acidic extracts were then made basic with 2N aqueous sodium hydroxide solution and thereafter extracted with four-separate portions of fresh chloroform. The final chloroform extracts were then combined and subsequently dried over anhydrous sodium sulfate, followed by filtration and concentration of the resulting filtrate with the aid of a rotary evaporator to ultimately yield 760 mg of free organic base product in the form of a residual oil. The latter material was then dissolved in ethyl acetate, and diethyl ether saturated with dry hydrogen chloride was next added to the solution. The resulting white solid product, which precipitated as the hydrochloride acid addition salt, was then collected by means of suction filtration and thereafter washed and dried with diethyl ether to eventually afford 600 mg. (6%) of pure (2S,3S)-cis-3-(2-methoxy-5-trifluoromethoxybenzyl)amino-2-phenylpiperidine hydrochloride, m.p. >250° C. The pure product was further characterized by means of high-resolution mass spectrum (HRMS) analysis and nuclear magnetic resonance (NMR) data, in addition to elemental analysis.

HRMS and NMR Data: The HRMS spectrum and $^1$H NMR spectrum were both found to be consistent with product.

Anal. Calcd. for C$_{20}$H$_{23}$F$_3$N$_2$O$_2$.2HCl.0.2H$_2$O: C, 52.57; H, 5.60, N, 6.13. Found: C, 52.58, H, 5.40; N, 5.97.

EXAMPLE 6

To a well-stirred solution consisting of 1.17 g (0.0040 mole) of (2S,3S)-2-(diphenylmethyl)-1-azabicyclo[2.2.2]octane-3-amine (prepared according to the procedure described by F. Ito et al., in aforementioned Published P.C.T. International Patent Application No. WO 92/21677) and 748 mg (0.0042 mole) of 2-methoxy-5-isopropylbenzaldehyde (the product of Example 4) dissolved in 40 mL methylene chloride while under a dry nitrogen atmosphere, there was added 933 mg (0.0044 mole) of sodium triacetoxyborohydride which was divided into small portions. The resulting reaction mixture was then stirred at room temperature (ca. 20° C.) until the organic amine starting material was slowly observed to disappear. At this point, the clear organic solution thus obtained was carefully neutralized with ice-chilled saturated aqueous sodium bicarbonate solution, thereby leading to the formation of two different phases. The organic layer was separated and saved, and thereafter washed with several portions of water and subsequently dried over anhydrous magnesium sulfate. After removal of the drying agent by means of suction filtration and the solvent by means of evaporation under reduced pressure, there were finally obtained 1.82 g (nearly-quantitative yield) of essentially pure (2S,3S)-cis-2-(diphenylmethyl)-N-[(2-methoxy-5-isopropylphenyl)methyl]-1-azabicyclo[2.2.2.]octane-3-amine as the residual product. Treatment of the latter organic base in an acetone solution with an equivalent amount of methanesulfonic acid then gave the corresponding mesylate salt in the form of a precipitate. The latter material was subsequently collected by means of suction filtration and dried in vacuo to constant weight to afford pure (2S,3S)-cis-2-(diphenylmethyl)-N-[(2-methoxy-5-isopropyl)methyl]-1-azabicyclo[2.2.2]octane-3-amine methanesulfonate, m.p. 221° C. The pure product was further characterized by means of infrared (IR) absorption spectral analysis and nuclear magnetic resonance (NMR) data.

IR and NMR Data: The IR spectrum and $^1$HNMR spectrum were both found to be consistent with product.

We claim:

1. A process for preparing a 5-substituted 2-methoxybenzaldehyde compound having the formula:

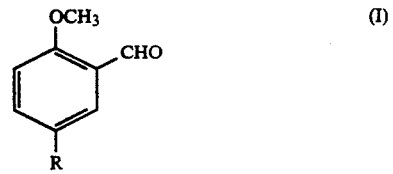

wherein R is isopropyl or trifluoromethoxy, which comprises the steps of
   (a) reacting a corresponding 4-substituted phenol compound of the formula:

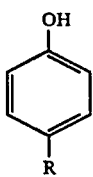

wherein R is as hereinbefore defined, with dimethyl carbonate in the presence of a tertiary-amine base and in the presence or absence of a reaction-inert polar organic solvent, with the proviso that said solvent is always present when R is isopropyl, said reaction being conducted at a temperature that is in the range of from about 120° C. up to about 170° C. until the O-methylation reaction to form the corresponding 4-substituted anisole compound of the formula:

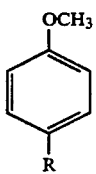

wherein R is as previously defined, is substantially complete; and (b) thereafter subjecting the intermediate 4-substituted anisole compound of the formula III obtained in step (a) to aromatic C-formylation on the ring by initially reacting said anisole compound at the desired ortho-position with hexamethylenetetramine in the presence of trifluoroacetic acid at a temperature that ranges from between about 65° C. and the reflux temperature of the reaction mixture until the ortho-substitution reaction is substantially complete, followed by hydrolysis of the resulting mixture at ambient temperatures by addition of water thereto to ultimately yield the desired aldehyde compound of structural formula I.

2. A process as claimed in claim 1 wherein R is trifluoromethoxy.

3. A process as claimed in claim 1 wherein R is isopropyl.

4. A process as claimed in claim 2 wherein the reaction in step (a) is carried out in the absence of a solvent.

5. A process as claimed in claim 3 wherein the reaction in step (a) is carried out in the presence of dimethyl sulfoxide.

6. A process as claimed in claim 1 wherein the molar ratio of the phenolic starting material of formula II to dimethyl carbonate reagent in step (a) ranges from about 1.0:1.0 to about 1.0:5.0, respectively.

7. A process as claimed in claim 6 wherein the amount of tertiary-amine base employed in step (a) ranges from about 20 mole percent up to about 80 mole percent, based on the total molar amount of phenolic starting material of formula II.

8. A process as claimed in claim 7 wherein the tertiary-amine base employed in step (a) is 4-dimethylaminopyridine.

9. A process as claimed in claim 1 wherein the molar ration of the intermediate starting compound of formula III to hexamethylenetetramine reagent in step (b) ranges from about 4.0:1.0 to about 1.0:2.0, respectively.

10. A process as claimed in claim 1 wherein the initial aromatic C-formylation reaction in step (b) is conducted at a temperature that lies within the range of from about 70° C. up to about 90° C.

* * * * *